United States Patent
Harks et al.

(10) Patent No.: US 10,537,428 B2
(45) Date of Patent: Jan. 21, 2020

(54) GUIDED DELIVERY OF PROSTHETIC VALVE

(75) Inventors: Godefridus Antonius Harks, Eindhoven (NL); Gert Wim 'T Hooft, Eindhoven (NL); Raymond Chan, San Diego, CA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 603 days.

(21) Appl. No.: 14/114,214

(22) PCT Filed: Apr. 23, 2012

(86) PCT No.: PCT/IB2012/052040
§ 371 (c)(1),
(2), (4) Date: Oct. 27, 2013

(87) PCT Pub. No.: WO2012/147028
PCT Pub. Date: Nov. 1, 2012

(65) Prior Publication Data
US 2014/0052241 A1    Feb. 20, 2014

Related U.S. Application Data

(60) Provisional application No. 61/479,995, filed on Apr. 28, 2011.

(51) Int. Cl.
*A61F 2/24* (2006.01)
*A61B 34/20* (2016.01)

(52) U.S. Cl.
CPC ............ *A61F 2/2427* (2013.01); *A61B 34/20* (2016.02); *A61B 2034/2061* (2016.02)

(58) Field of Classification Search
CPC .................................................. A61F 2/2427
See application file for complete search history.

(56) References Cited

U.S. PATENT DOCUMENTS

| 8,442,618 | B2 | 5/2013 | Strommer et al. |
| 9,232,982 | B2 | 1/2016 | Wolfisheim et al. |
| 2004/0049266 | A1* | 3/2004 | Anduiza ............... A61F 2/2418 623/2.11 |

(Continued)

FOREIGN PATENT DOCUMENTS

| DE | 102009009158 | 9/2010 |
| EP | 1173105 A1 | 1/2002 |

(Continued)

*Primary Examiner* — Richard G Louis (57) ABSTRACT

An image-guided prosthetic valve deployment system employs a prosthetic valve (80), a catheter (70) and a delivery tracking system (90). The catheter (70) has an elongated body with a proximal tip (71*a*) and a distal tip (71*b*), and the elongated body includes a delivery section (72) adjacent the distal tip (71*b*) for deploying the prosthetic valve (80) relative to a heart valve (21) within an anatomical region (20). The delivery section (72) includes a delivery segment (73) for sensing a shape and an orientation of the delivery section (72) within the anatomical region (20) relative to a reference point (74). The delivery tracking system (90) tracks a position and an orientation of the prosthetic valve (80) relative to the heart valve (21) as a function of a sensed shape and a sensed orientation of the delivery section (72) within the anatomical region (20) relative to the reference point (74) by the delivery segment (73).

11 Claims, 8 Drawing Sheets

(56) References Cited

U.S. PATENT DOCUMENTS

| | | |
|---|---|---|
| 2004/0097804 A1 | 5/2004 | Sobe |
| 2004/0171924 A1* | 9/2004 | Mire ................ G06F 19/3437 |
| | | 600/407 |
| 2005/0228274 A1* | 10/2005 | Boese ............... A61M 25/0105 |
| | | 600/433 |
| 2007/0088431 A1 | 4/2007 | Bourang et al. |
| 2007/0106115 A1* | 5/2007 | Sugimoto ................ A61B 1/31 |
| | | 600/117 |
| 2008/0097210 A1* | 4/2008 | Salgo et al. .................. 600/445 |
| 2008/0059149 A1 | 6/2008 | Gersak et al. |
| 2008/0285909 A1* | 11/2008 | Younge ................ A61B 5/1076 |
| | | 385/13 |
| 2009/0259296 A1* | 10/2009 | McIff ....................... A61B 5/06 |
| | | 623/1.34 |
| 2009/0319037 A1* | 12/2009 | Rowe et al. .................. 623/2.11 |
| 2010/0198346 A1* | 8/2010 | Keogh ................... A61B 34/20 |
| | | 623/2.11 |
| 2011/0046725 A1* | 2/2011 | Noettling .............. A61B 6/032 |
| | | 623/2.11 |
| 2011/0249794 A1 | 10/2011 | Florent |
| 2012/0141142 A1 | 6/2012 | Ishaug et al. |
| 2012/0290078 A1 | 11/2012 | Bourang et al. |
| 2014/0052241 A1 | 2/2014 | Harks et al. |

FOREIGN PATENT DOCUMENTS

| | | |
|---|---|---|
| EP | 2260784 | 12/2010 |
| WO | 2009023801 | 2/2009 |
| WO | 2009148317 A1 | 12/2009 |
| WO | WO2009148317 | 12/2009 |

\* cited by examiner

GUIDED DELIVERY OF PROSTHETIC VALVE

CROSS-REFERENCE TO PRIOR APPLICATIONS

This application is the U.S. National Phase application under 35 U.S.C. § 371 of International Application Serial No. PCT/IB2012/052040, filed on Apr. 23, 2012, which claims the benefit of U.S. Application Ser. No. 61/479,995, filed on Apr. 28, 2011. These applications are hereby incorporated by reference herein.

The present invention generally relates to the delivery of a prosthetic valve during a heart valve replacement procedure guided by localization during device deployment. The present invention specifically relates to a utilization of both a reference element and a shape sensor for determining a proper positioning and orientation of the prosthetic valve relative the heart valve.

Aortic stenosis is the most frequent acquired cardiac valve disease requiring hospitalization. Open-heart surgery to address the disease may provide excellent and durable results, but many fragile patients are not eligible to undergo this procedure due to their poor condition. Minimally-invasive transcatheter valve replacement is a relatively new and promising alternative for this large population of patients. The valve replacement procedure delivers a prosthetic valve to the patient's native valve annulus, and then expands the prosthesis over the native valve.

One of the critical steps in transcatheter valve replacement is the deployment of the prosthetic valve at the proper position and orientation with respect to the native valve annulus and the ostia of the coronary arteries. This deployment is critical, because occlusion of the coronary ostia due to misdirected prosthetic valve deployment may lead to myocardial ischemia and infarction. Therefore, real-time information about the position and orientation of the prosthetic device during deployment may significantly reduce complications and increase clinical throughput.

Clear visualization of the full valve annulus and the delivery device may be very difficult to achieve with fluoroscopy alone and may be no less challenging with a transesophageal ("TEE") probe if the valve leaflets are highly calcified. Typically, the physician identifies the aortic valve orifice on fluoroscopy using aortography and the visible calcium deposits on the valve. The C-arm is then positioned so that all three valve sinuses of the aortic annulus are in the same imaging plane. Thus, the valve annulus and delivery device are visualized in 2D, whereas 3D information of the orientation and position of the prosthetic valve relative to the annulus would be desired.

After navigating the prosthetic valve through the native valve annulus into the left ventricle with the delivery catheter, the prosthetic valve (optionally mounted on balloon) is pulled back over the guidewire into the native valve annulus at the preferred orientation and position. Then, the valve is deployed (optionally by inflating a delivery balloon) and the prosthetic valve is pressed firmly against the valve annulus, limiting recoil of the native valve and reducing paravalvular leakage. Valve deployment is monitored with fluoroscopy and/or TEE. After deployment, the valve implant is assessed using TEE and/or aortography to check for proper blood flow into the coronary arteries (no obstruction) and for paravalvular regurgitation. The blood pressure in the aorta is also checked.

The present invention provides a guided valve replacement system and method for deployment of the prosthetic valve at the proper position and orientation with respect to the native valve annulus.

One form of the present invention is a guided prosthetic valve deployment system employing a prosthetic valve, a catheter, and a delivery tracking system. The catheter has an elongated body with a proximal tip and a distal tip, the elongated body including a delivery section adjacent the distal tip for deploying the prosthetic valve relative to a heart valve within an anatomical region. The delivery section includes a delivery segment for sensing a shape and an orientation of the delivery section within the anatomical region relative to a reference element. The delivery tracking system tracks a position and an orientation of the prosthetic valve relative to the heart valve as a function of a sensed shape and a sensed orientation of the delivery section within the anatomical region relative to the reference element as sensed by the delivery segment.

A second form of the present invention is a guided prosthetic valve deployment method involving navigation of a catheter within an anatomical region, the catheter having an elongated body with a proximal tip and a distal tip, the elongated body including a delivery section adjacent the distal tip for deploying a prosthetic valve relative to a heart valve within the anatomical region. The method further involves a sensing of a shape and an orientation the delivery section within the anatomical region relative to a reference element as the catheter is navigated within the anatomical region, and a tracking of a position and an orientation of the prosthetic valve relative to the heart valve as a function of the sensed shape and the sensed orientation of the delivery section within the anatomical region relative to the reference element sensed by the delivery segment.

The foregoing forms and other forms of the present invention as well as various features and advantages of the present invention will become further apparent from the following detailed description of various exemplary embodiments of the present invention read in conjunction with the accompanying drawings. The detailed description and drawings are merely illustrative of the present invention rather than limiting, the scope of the present invention being defined by the appended claims and equivalents thereof.

Figure 1:
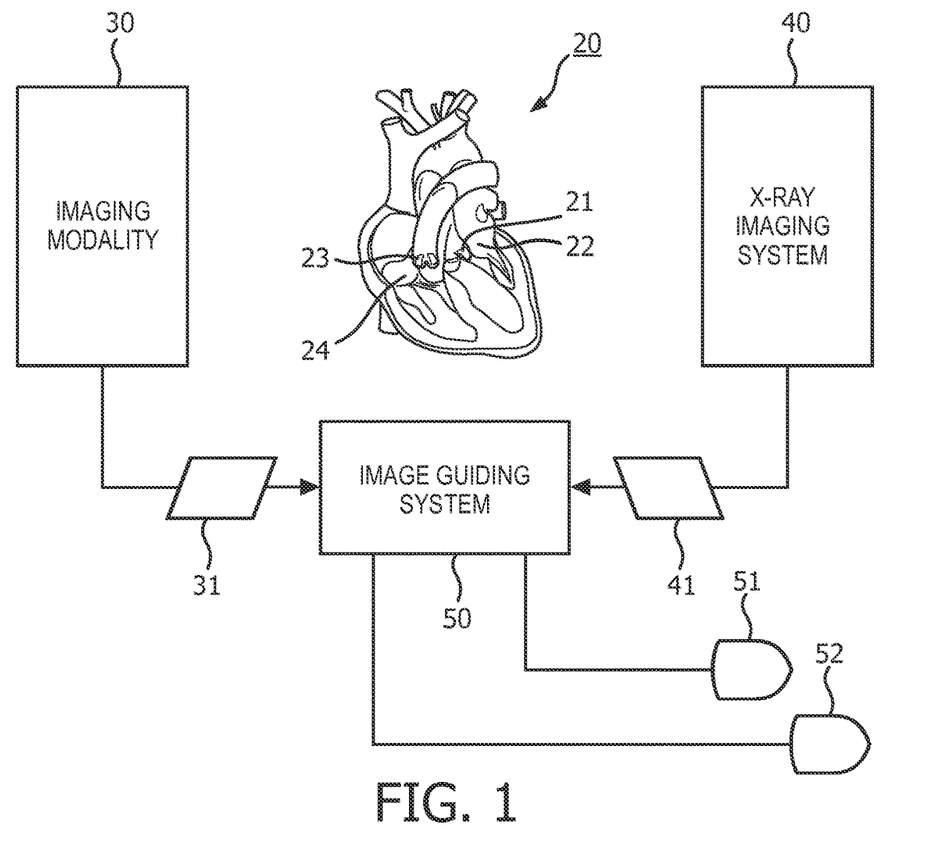
FIG. 1 illustrates a block diagram of an exemplary embodiment of a heart valve imaging system in accordance with the present invention.
Figure 2:
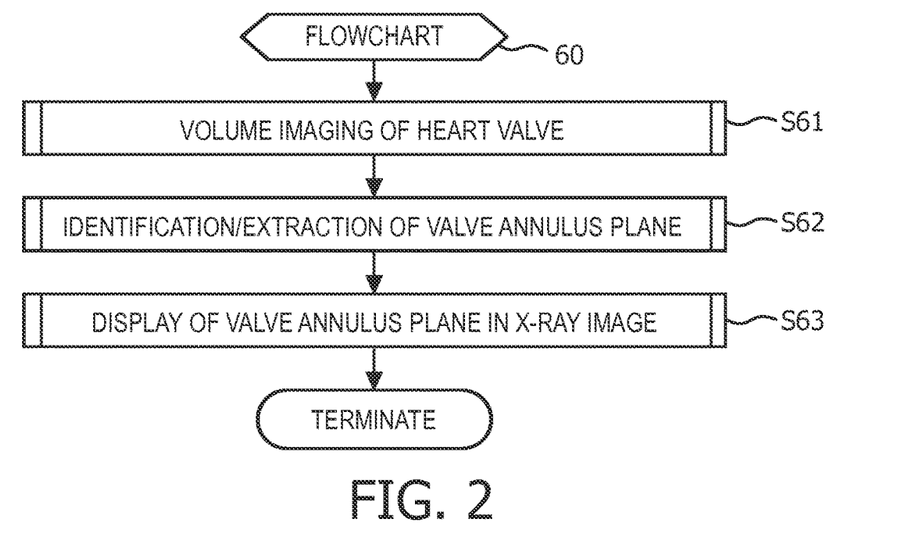
FIG. 2 illustrates a flowchart representative of an exemplary embodiment of a heart valve imaging method in accordance with the present invention.

As shown in FIG. 1, a heart valve imaging system of the present invention employs an imaging modality 30, an X-ray imaging system 40 and an image guiding system 50 for displaying a valve annulus plane relative to a diseased or otherwise damaged heart valve in accordance with a flowchart 60 as shown in FIG. 2.

For purposes of the present invention, the term "valve annulus plane" is broadly defined as any plane that traverses across an annulus of an associated heart valve. For example, FIG. 1 illustrates a heart 20 having four (4) valves in the form of an aortic valve 21, a mitral valve 22, a pulmonary valve 23 and a tricuspid valve 24. A valve annulus plane of aortic valve 21 would therefore be any plane traversing across an annulus of aortic valve 21. In practice, the preferred valve annulus plane of a heart valve for purposes of the present invention will be dependent upon the particulars of the corresponding valve replacement procedure.

Referring to FIGS. 1 and 2, a valve replacement procedure for heart 20 requires a prosthetic valve being properly positioned and oriented relative to the diseased/damaged heart valve among one of the heart valves 21-24 being replaced. To this end during a pre-operative or intra-operative stage S61 of flowchart 60, imaging modality 30 generates a three-dimensional ("3D") volume image of an annulus of the diseased/damaged heart valve as known in the art and communicates a dataset 31 representative of the volume image to image guiding system 50. In practice, imaging modality 30 may be any imaging modality structurally configured for generating 3D volume images. Examples include, but are not limited to, a magnetic resonance imaging system, a computerized tomography system and a 3D ultrasound system. Also in practice, the visual scope of the volume image of the heart valve will be dependent upon the particular heart valve replacement procedure being implemented by flowchart 60.

Figure 3A:
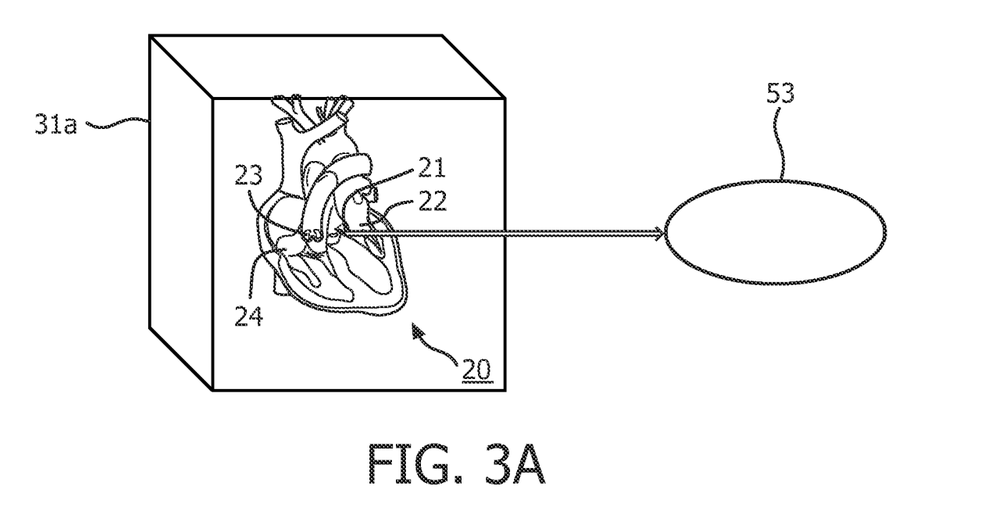
FIGS. 3A and 3B illustrate an exemplary display of a valve annulus plane overlay on an X-ray image of a heart valve in accordance with the present invention.

During a pre-operative or intra-operative stage S62 of flowchart 60, image guiding system 50 is structurally configured with hardware, software and/or firmware for extracting a valve annulus plane associated with the diseased/damaged heart valve from within the volume image of the diseased/damaged heart valve. In one embodiment, image guiding system 50 utilizes a model of heart 20 as a basis for identifying the valve annulus plane and then extracting the valve annulus plane from the volume image of the heart valve. For example, as shown in FIG. 3A, a valve annulus plane 53 may be extracted from a volume image 31a of heart 20 based on an identification of valve annulus plane 53 within a model of heart 20 or any other comparable heart.

Figure 3B:
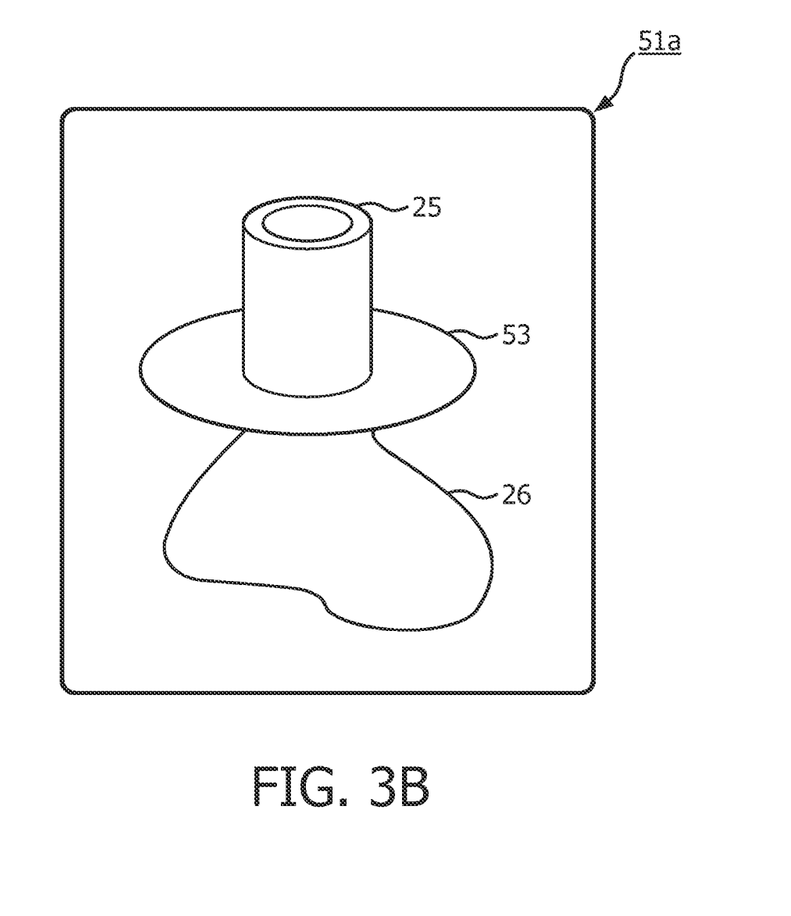

During an intra-operative stage S63 of flowchart 60, X-ray imaging system 40 generates an X-ray image of the diseased/damaged heart valve as known in the art and communicates a dataset 41 representative of the X-ray image to image guiding system 50. In turn, image guiding system 50 is further structurally configured with hardware, software and/or firmware for generating a display 51 of an overlay of the extracted valve annulus plane in the X-ray image of the heart valve. For example, as shown in FIG. 3B, a display 51a illustrates an X-ray image of an aorta 25 extending from a left ventricle 26 and encircled by an overlay of valve annulus plane 53 associated with an annulus of aortic valve 21 (not shown).

Imaging guiding system 50 may further be structurally configured with hardware, software and/or firmware for generating a display 52 (FIG. 1) of an orientation of the prosthetic valve to the valve annulus plane of the heart valve. Embodiments of display 52 will be described subsequently herein in connection with a description of FIGS. 11A and 11B.

In practice, image guiding system 50 may be incorporated within image modality 30, X-ray system 40 or within a separate workstation.

Figure 4:
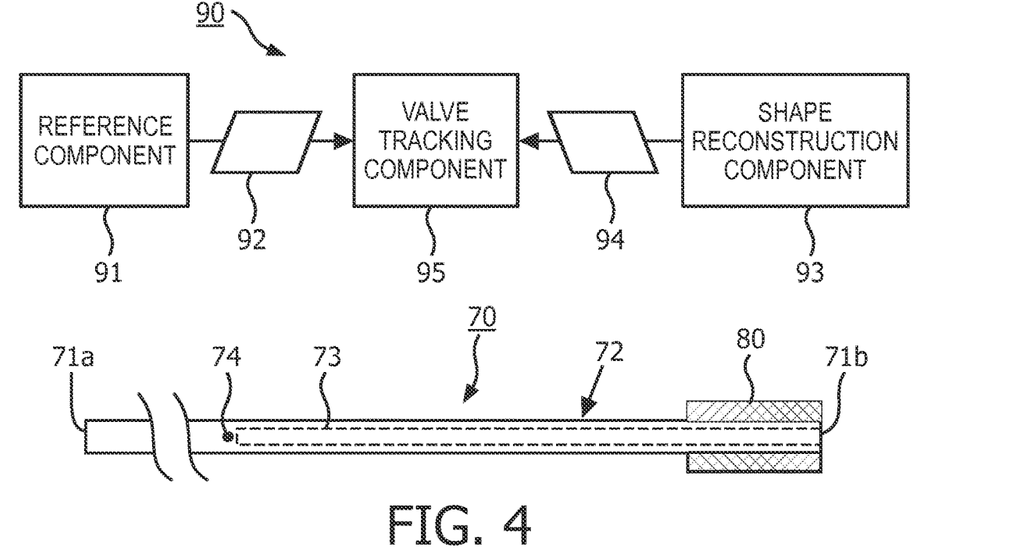
FIG. 4 illustrates a block diagram of an exemplary embodiment of a delivery tracking system in accordance with the present invention.
Figure 7:
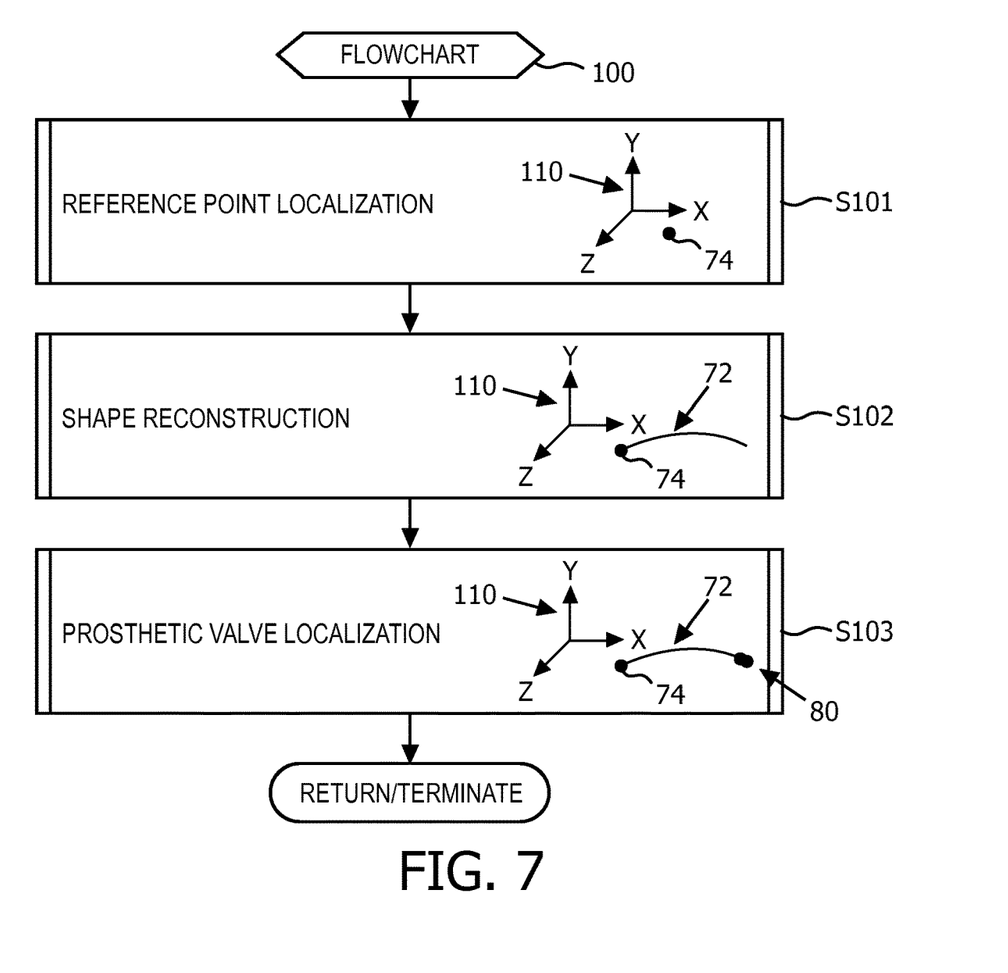
FIG. 7 illustrates a flowchart representative of an exemplary embodiment of a delivery tracking method in accordance with the present invention.

As shown in FIG. 4, a delivery tracking system 90 employs a reference component 91, a shape reconstruction component 93 and a valve tracking component 95 in accordance with a flowchart 100 as shown in FIG. 7 for tracking a prosthetic valve 80 as a catheter 70 is deployed during a heart valve replacement procedure.

Catheter 70 is equipped with a tubular body 71 extending from a proximal 71a to a distal tip 71b with a delivery section 72 being adjacent distal tip 71b (i.e., delivery section 72 is closest to the distal tip 71b than proximal tip 71a). Integrated within a delivery section 72 of tubular body 71 is a delivery segment 73 for sensing a shape and orientation of delivery section 72 relative to a reference element 74. In practice, reference element 74 may be a subsegment located along any position of delivery section 72, such as, for example, adjacent a proximal end of delivery segment 73.

Reference component 91 is structurally configured as known in the art for localizing a position and orientation of reference element 74 within an anatomical region like heart 20 (FIG. 1). In practice, the embodiment of reference component 92 is dependent upon the type of delivery segment 73 being utilized for the procedure.

Shape reconstruction unit 93 is structurally configured as known in the art for reconstructing a shape of delivery section 72. Similarly, in practice, the embodiment of shape reconstruction unit is dependent upon the type of delivery segment 73 being utilized for the procedure.

Figure 5A:
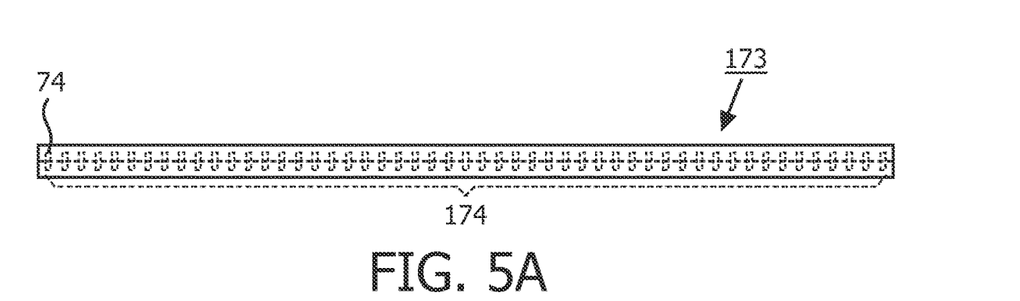
FIGS. 5A-5C illustrate exemplary embodiments of delivery segment in accordance with the present invention.

Specifically, in one embodiment 173 of delivery segment 73 as shown in FIG. 5A, delivery segment 173 is an optical fiber broadly defined herein as any article or device structurally configured for transmitting light by means of successive internal optical reflections via one or more deformation sensor arrays 174 with the proximal end of delivery segment 173 defining reference point 74. For purposes of the present invention, each deformation optic sensor of array 174 is broadly defined herein as any article structurally configured for reflecting a particular wavelength of light while transmitting all other wavelengths of light whereby the reflection wavelength may be shifted as a function of an external stimulus applied to optical fiber 173.

An example of optical fiber 173 and deformation optic sensor array 174 is a flexible optically transparent glass or plastic fiber having fiber Bragg gratings integrated along a length of the fiber as known in the art.

Another example of optical fiber 173 and deformation optic sensor array 174 is a flexible optically transparent glass or plastic fiber having naturally random variations in its optic refractive index occurring along a length the fiber as known in the art whereby the random fluctuations may be modeled as fiber Bragg gratings with a random variation of amplitude and phase along the grating length.

For delivery segment 173, reference component 91 may be a magnetic resonance localization unit, an ultrasound-based localization unit, or a direct X-ray imaging/processing unit for purposes of localizing reference element 74 as known in the art. In addition, shape reconstruction unit 93 may an optical console for reconstructing a shape of array 174 as known in the art.

Figure 5B:
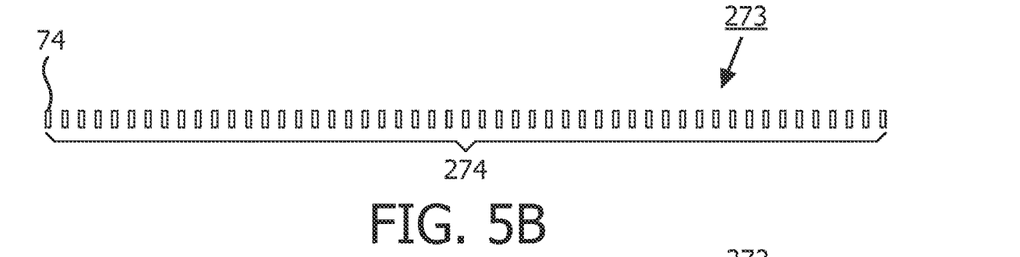

In another embodiment 273 of delivery segment 73 as shown in FIG. 5B, delivery segment 273 is an electromagnetic sensor having an array 274 of electromagnetic coils with a proximal end of array 274 defining reference point 74.

For delivery segment 273, reference component 91 may be a six degrees-of-freedom ("6 DOF") electromagnetic tracking unit or a 6 DOF impedance localization unit for purposes of localizing reference element 74 as known in the art. In addition, shape reconstruction unit 93 may be a separate or integrated 6 DOF electromagnetic tracking unit or a 6 DOF impedance localization unit for reconstructing a shape of array 274 as known in the art.

Figure 5C:
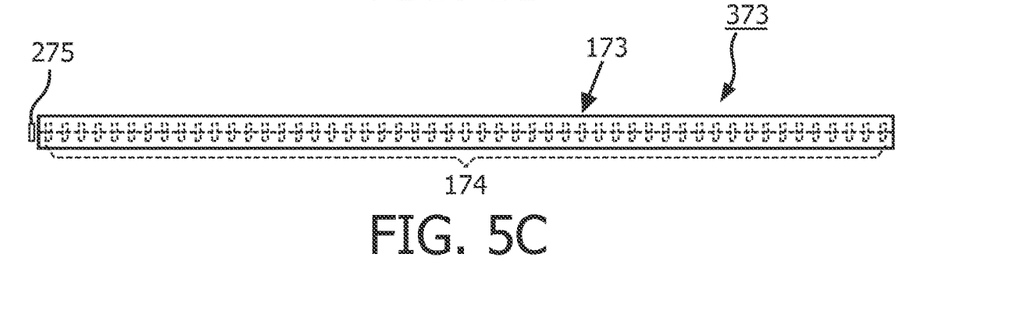

In yet another embodiment 373 of delivery segment 73 as shown in FIG. 5C, delivery segment 373 includes optical fiber 173 and an electromagnetic coil 275 defining reference element 74.

For delivery segment 373, reference component 91 may be a six degrees-of-freedom ("6 DOF") electromagnetic tracking unit or a 6 DOF impedance localization unit for purposes of localizing electromagnetic coil 275 as known in the art. In addition, shape reconstruction unit 93 may be an optical console for reconstructing a shape of array 174 as known in the art.

Referring back to FIG. 4, prosthetic valve 80 is mounted adjacent to distal tip 61b. However, in practice, prosthetic valve 80 will be mounted to delivery section 72 in dependence upon the particulars of the heart valve replacement procedure.

Figure 6:
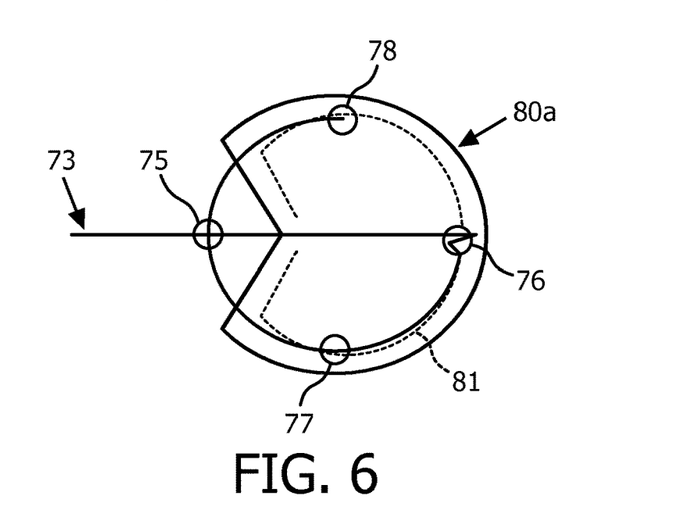
FIG. 6 illustrates a schematic diagram of an exemplary embodiment of a prosthetic valve mounted on a delivery section of a catheter in accordance with the present invention.

In one embodiment as shown in FIG. 6, a prosthetic valve 80a with embedded delivery segment 73 circumscribes a valve annulus. In the shown undeployed state, prosthetic valve 80a is folded over a deployment balloon 81 and a distal segment of delivery segment 73 is coiled up in a collapsed state. After deployment, prosthetic valve 80a is expanded and delivery segment 73 is uncoiled to extend over the annulus in the deployed state. The circumscribing segment of delivery segment 73 defines the valve plane and annulus orientation. The tip of that segment may be designed to coincide with the centerpoint of the non-coronary cusp, with each of the coronary cusps annotated based on angular position along the curved segment of delivery segment 73. Curve locations 75-78 correspond to anatomical features (e.g., coronary ostia).

Flowchart 100 as shown in FIG. 7 will now be described herein to facilitate an understanding of valve tracking module 95 of FIG. 5.

During an intra-operative stage S101 of flowchart 100, reference component 91 localizes a position and orientation of reference element 74 within a global reference coordinate system 110 registered with an image of heart 20 as known in the art, and communicates a dataset 92 representative of the localized position and orientation of reference element 74 to valve tracking module 95. During an intra-operative stage S102 of flowchart 100, shape reconstruction unit 93 reconstructs a shape of delivery section 72 within global reference coordinate system 110 as known in the art and communicates a dataset 94 representative of the reconstructed shape of delivery section 72 within global reference coordinate system 110 to valve tracking module 95.

During an intra-operative stage S103 of flowchart 100, valve tracking module 95 is structurally configured with hardware, software and/or firmware for processing datasets 92 and 94 to thereby localize a position and an orientation of prosthetic valve 80 relative to the heart valve within global reference coordinate system 110. Specifically, valve tracking module 95 has knowledge of the particular design of delivery section 72 in terms of the spatial relationship between delivery segment 73 and reference point 74 and the spatial relationship between delivery segment 73 and prosthetic valve 80. As such, valve tracking module 95 processes datasets 81 and 91 to determine the local position and rotational orientation of delivery section 72 within global reference coordinate system 110 relative to the heart valve (not shown).

In practice, valve tracking module 95 may be incorporated within reference component 91, within shape reconstruction unit 93, within image guiding system 50 (FIG. 1), or within a separate workstation.

Figure 8:
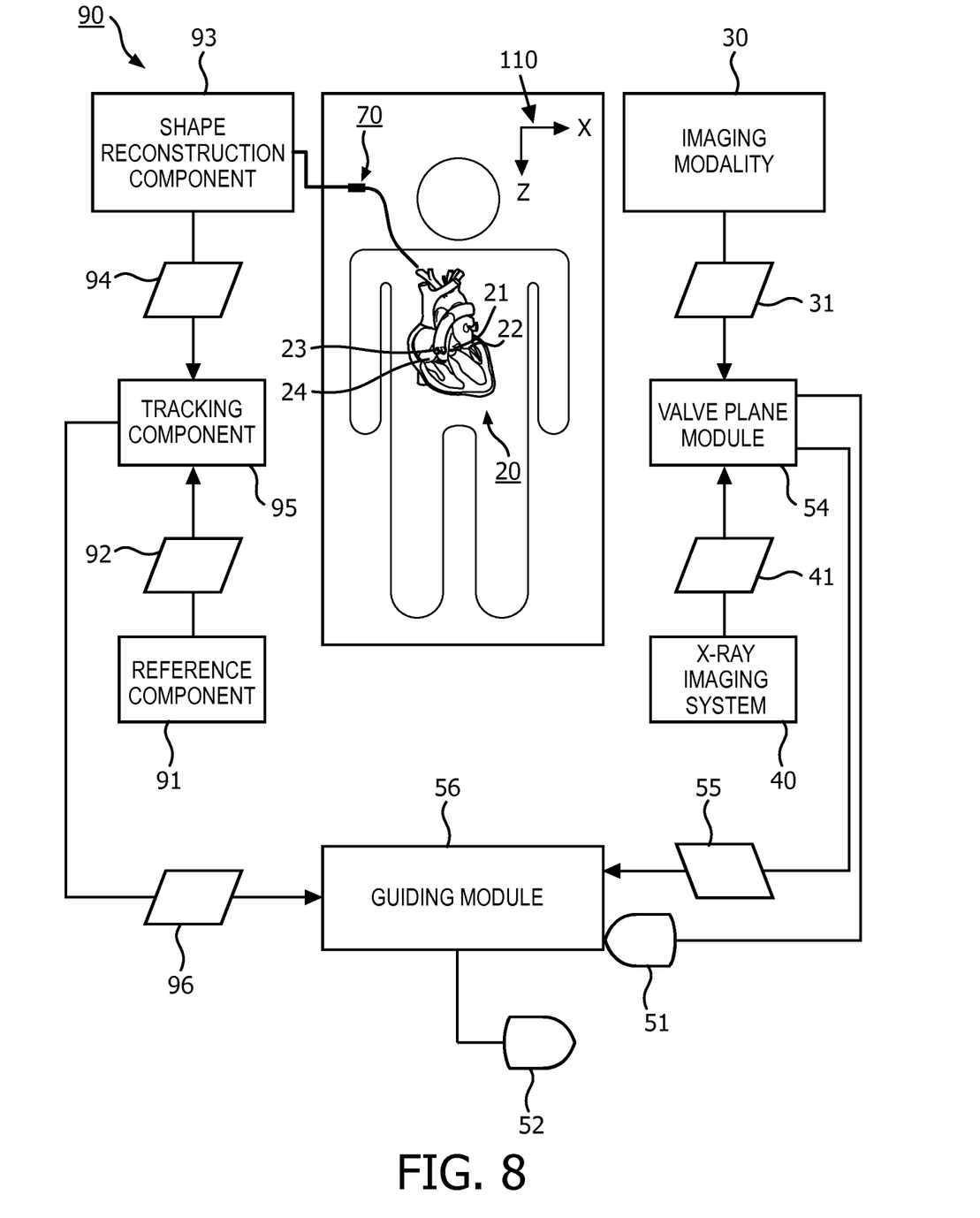
FIG. 8 illustrates a block diagram of an exemplary embodiment of an image-guided prosthetic valve deployment system in accordance with the present invention.
Figure 9:
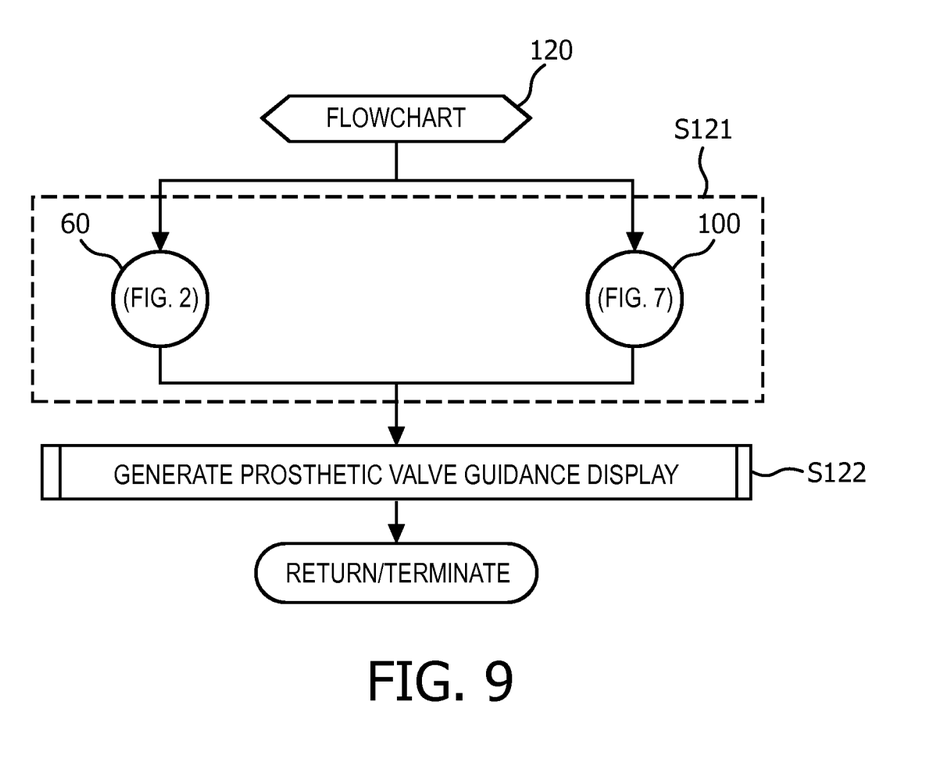
FIG. 9 illustrates a flowchart representative of an exemplary embodiment of an image-guided prosthetic valve deployment method in accordance with the present invention.

FIG. 8 illustrates an image-guided valve replacement system employing the image guiding system 50 of FIG. 1 including a valve plane module 54 and a guiding module 56, and the delivery tracking system 90 of FIG. 4 whereby tracking component 95 generates a dataset 96 of the determined local position and rotational orientation of delivery section 72 within global reference coordinate system 110. System 50 and 90 implement a flowchart 120 as shown in FIG. 9 for facilitating a proper positioning and orientation of prosthetic valve 80 (FIG. 4) relative to a diseased or otherwise damaged heart valve of heart 20.

Specifically, a first phase 121 of flowchart 120 involves an implementation of flowchart 60 of FIG. 2 by image guiding system 50 and an implementation of flowchart 100 of FIG. 7 by delivery tracking system 90. In practice, stages S61 and S62 of flowchart 60 may be performed prior to an insertion of catheter 70 within the patient while stage S63 of flowchart 60 as well as all stages of flowchart 100 are performed in real-time. Also in practice, system 50 or system 80 may be utilized to establish global reference coordinate system 110 (of which only an XZ plane is shown in FIG. 8).

During a stage S122 of flowchart 120, a valve plane module 54 is structurally configured with hardware, software and/or firmware for extracting the valve annulus plane associated with the diseased/damaged heart valve from within a volume image of the diseased/damaged heart valve. Valve plane module 54 communicates a display 51 of an overlay of the extracted valve annulus plane in an X-ray image of the heart valve and/or a dataset 55 of the extracted valve annulus plane to guiding module 56. In turn, guiding module 56 is structurally configured with hardware, software and/or firmware for generating a prosthetic valve guidance display 52 illustrating a positioning and/or an orientation of the prosthetic valve relative to the heart valve as catheter 70 is navigated within heart 20.

Figure 10A:
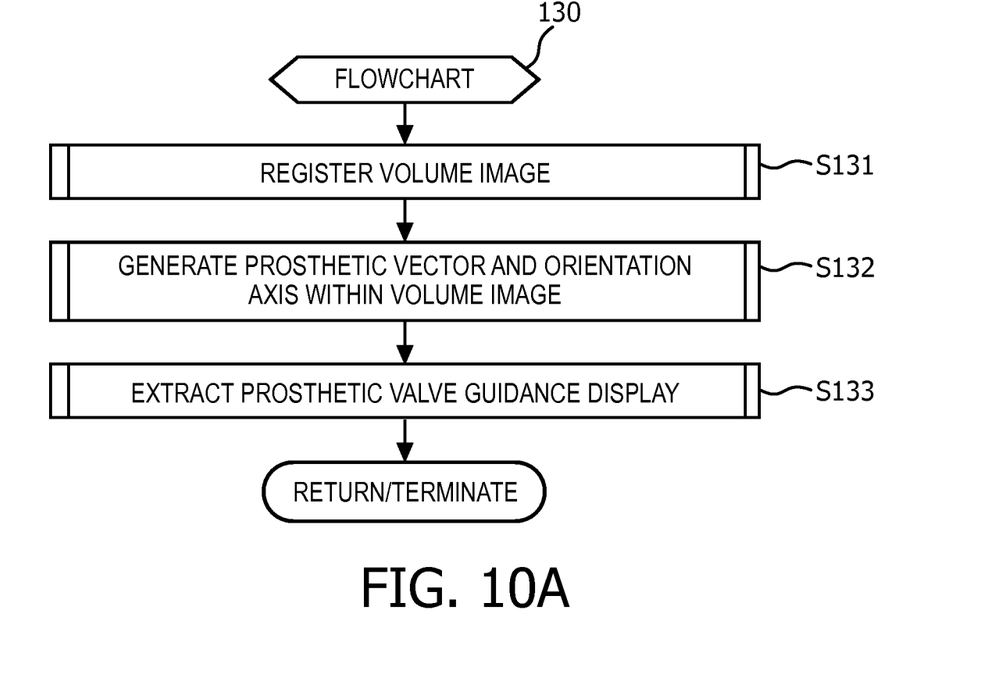
FIGS. 10A and 10B illustrate flowcharts representative of exemplary embodiments of a prosthetic valve guidance display method in accordance with the present invention.

In one embodiment of stage S122 as shown in FIG. 10A, guiding module 56 registers the volume image of the heart valve with global reference coordinate system 110 during a stage S131 of a flowchart 130, generates a prosthetic vector and orientation axis within the volume image during a stage S132 of flowchart 130 and extracts the prosthetic valve guidance display during a stage S133 of flowchart 130.

Figure 11A:
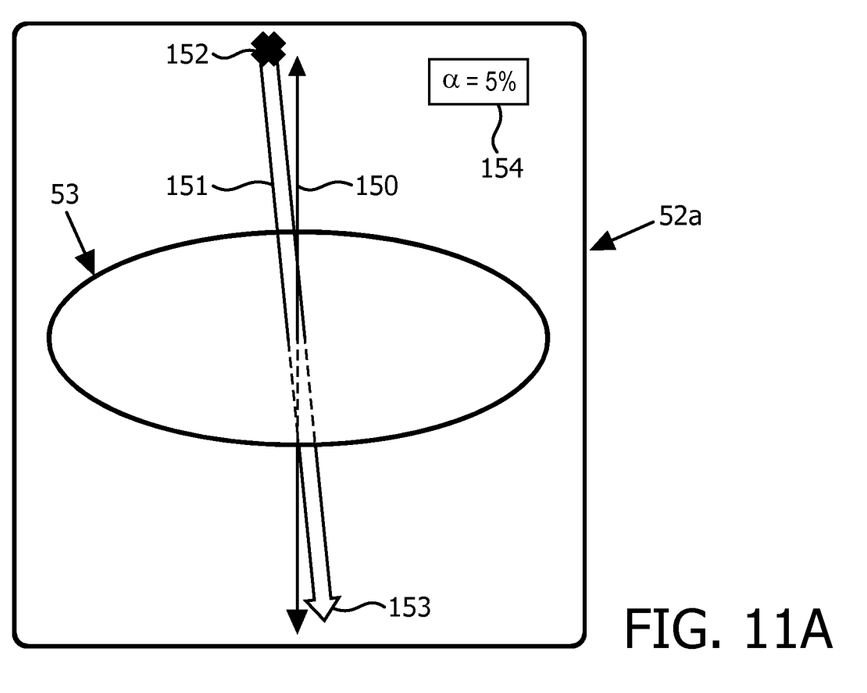
FIGS. 11A and 11B illustrate exemplary displays of an angular orientation of prosthetic vector relative to a valve annulus plane in accordance with the present invention.

FIG. 11A illustrates one example of a prosthetic valve guidance display 52a illustrating valve annulus plane 53, an orientation axis 150 extending perpendicularly through valve annulus plane 53, and a prosthetic vector 151 extending from reference point 152 through valve annulus plane 53 with a direction arrow 153 of prosthetic vector 151 symbolizing the prosthetic valve. Display 52a further illustrates an angular differential value 154 between orientation axis 150 and prosthetic vector 151.

The generation of display 52a provides a guidance tool during the heart valve replacement procedure whereby a proper positioning and orientation of the prosthetic valve may be accomplished. In particular, the catheter may be navigated within the heart with the goal of having angular differential value 154 equal to zero and to have the direction arrow 153 a proper distance from valve annulus plane 53.

While the body of prosthetic vector 151 essentially represents the delivery segment, the delivery segment may have an arc or curvy shape as the catheter is being navigated within heart. Nonetheless, in practice, the body of prosthetic vector 151 may be given a straight shape as shown based on the actual orientation of the prosthetic valve to orientation axis 150, or the actual shape of the delivery segment may be shown in display 52a.

Also in practice, display 52a may be 3D or two-dimensional ("2D") and may include features of the heart valve and surrounding heart tissue.

Figure 11B:
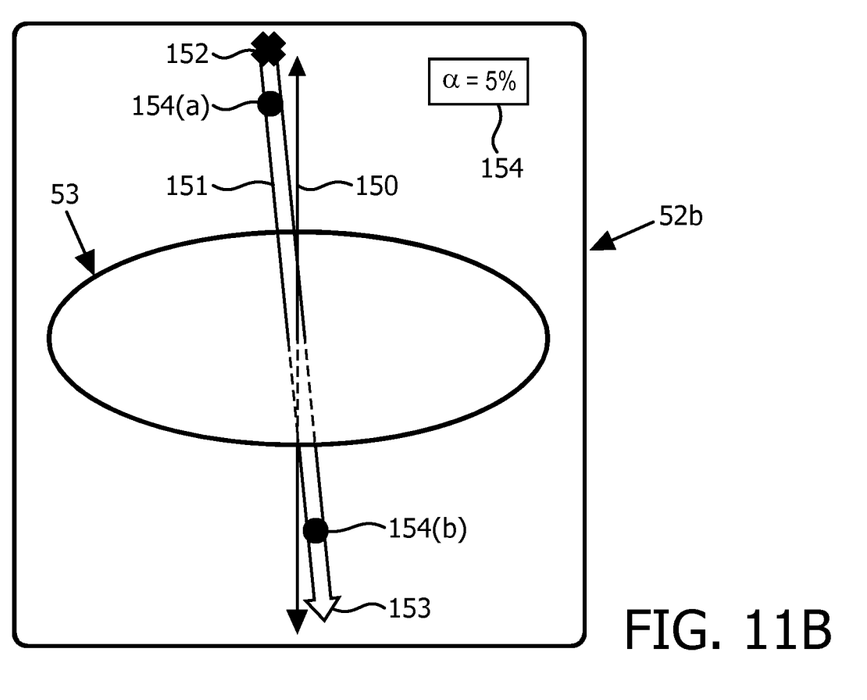

FIG. 11B illustrates an alternative version 52b of display 52a whereby markers 154(a) and 154(b) represent physiological parameters derived from the delivery segment (e.g., from FGB sensors) with each parameter providing color coded information or shape coded information. Examples of the physiological parameters include, but are not limited to, pressure in the aorta (e.g., marker 154(a)), pressure in the ventricle (e.g., marker 154(b)), and a paravalvular flow.

Figure 10B:
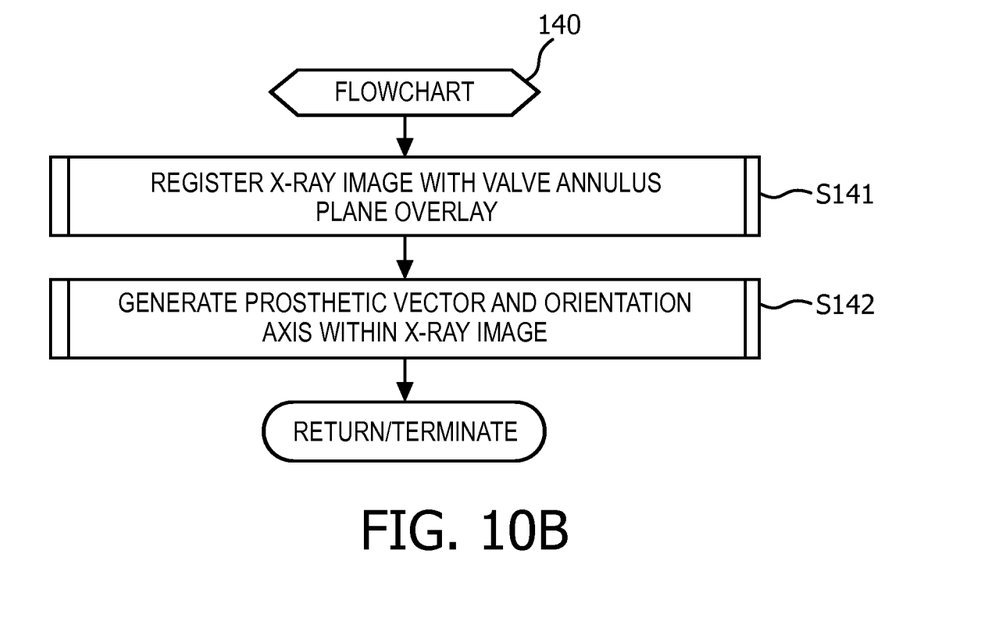

In a second embodiment of stage S132 (FIG. 10A) as shown in FIG. 10B, guiding module 56 registers the X-ray image of the heart valve having the overlay of the valve annulus plane within the global reference coordinate system 110 during a stage S141 of flowchart 140, and generates the prosthetic vector and the orientation axis within the X-ray image during a stage S142 of flowchart 140. For example, orientation axis 150 and prosthetic vector 151 of FIGS. 11A and 11B may be generated within X-ray image 51a of FIG. 3B.

From the description of FIGS. 1-11, those having skill in the art will have an appreciation on how to implement any suitable type of interventional procedure in accordance with the various image-guided techniques of the present invention. Specifically, any type of elongated interventional instrument (e.g., catheters, basket catheters, balloon catheters, leads, guidewires, sheaths, endoscopes, ablation catheters, arthroscopic systems, orthopedic implants, spinal implants, deep-brain stimulator (DBS) probes, drug delivery systems, mapping catheters, drill bits, stylets, trocars, screws or combinations thereof.) may be utilized to navigate any anatomical region (e.g., a heart, a bronchial tree, an abdomen, etc.) for delivery of any type of therapeutic device (e.g., a prosthetic valve, a stent, filter device, balloon, ablation device, atherectomy device, cooling device, a pacing device, electrode, or other implantable/prosthesis, etc.) relative to an anatomical object (e.g., a heart valve, a vessel, an endoluminal space, a virtual space (fascial layer) such as the perineum, pericardium, an interstitial target inside a tumor or other solid organ, a neuroanatomical target, etc.).

While various exemplary embodiments of the present invention have been illustrated and described, it will be understood by those skilled in the art that the exemplary embodiments of the present invention as described herein are illustrative, and various changes and modifications may be made and equivalents may be substituted for elements thereof without departing from the true scope of the present invention. For example, although the invention is discussed herein with regard to FBGs, it is understood to include fiber optics for shape sensing or localization generally, including, for example, with or without the presence of FBGs or other optics, sensing or localization from detection of variation in one or more sections in a fiber using back scattering, optical fiber force sensing, fiber location sensors or Rayleigh scattering. In addition, many modifications may be made to adapt the teachings of the present invention without departing from its central scope. Therefore, it is intended that the present invention not be limited to the particular embodiments disclosed as the best mode contemplated for carrying out the present invention, but that the present invention includes all embodiments falling within the scope of the appended claims.

The invention claimed is:

1. An image-guided prosthetic valve deployment system, comprising:
   a prosthetic valve;
   a catheter having an elongated body with a proximal tip and a distal tip, the elongated body including a delivery section adjacent the distal tip for deploying the prosthetic valve relative to a heart valve within an anatomical region,
      wherein the delivery section includes a delivery segment operable for sensing a shape and an orientation of the delivery section within the anatomical region relative to a reference element located at a position along the delivery section, and
   wherein the delivery segment includes:
      an optical fiber including a deformation sensor optic array operable for sensing the shape and the orientation of the delivery section within the anatomical region relative to the reference element; and
      an electromagnetic coil for defining the reference element;
   a delivery tracking system in communication with the delivery segment to track a position and an orientation of the prosthetic valve relative to the heart valve as a function of a sensed shape and a sensed orientation of the delivery section within the anatomical region relative to the reference element as sensed by the delivery segment; and
   an image guiding system in communication with the delivery tracking system to display an orientation of the prosthetic valve relative to a valve annulus plane of the heart valve derived from at least one of the sensed shape and the sensed orientation of the delivery section within the anatomical region relative to the reference element,
      wherein the valve annulus plane is extracted from within a volume image of the anatomical region excluding the prosthetic valve.

2. The image-guided prosthetic valve deployment system of claim 1,
   wherein the delivery segment is an optical fiber including a deformation sensor optic array operable for sensing the shape and the orientation of the delivery section within the anatomical region relative to the reference element; and
   wherein the deformation sensor array defines the reference element.

3. The image-guided prosthetic valve deployment system of claim 1, wherein a display of the orientation of the prosthetic valve relative to the valve annulus plane of the heart valve includes:
   a display the prosthetic valve relative to the valve annulus plane of the heart valve within an X-ray image of the anatomical region.

4. The image-guided prosthetic valve deployment system of claim 1, wherein the delivery segment at least partially circumscribes the prosthetic valve.

5. The image-guided prosthetic valve deployment system of claim 1, wherein a display of the orientation of the prosthetic valve relative to the valve annulus plane of the heart valve includes:
a display of an orientation axis perpendicular to the valve annulus plane; and
a display of an angular orientation of a prosthetic vector relative to the orientation axis, the prosthetic vector being representative of the position and the orientation of the prosthetic valve relative to the heart valve.

6. The image-guided prosthetic valve deployment system of claim 5, wherein a display of the orientation of the prosthetic valve relative to the valve annulus plane of the heart valve includes:
a display of an angular differential value between the orientation axis and the prosthetic vector.

7. An image-guided therapeutic device deployment system, comprising:
a therapeutic device;
an interventional instrument having an elongated body with a proximal tip and a distal tip, the elongated body including a delivery section adjacent the distal tip for deploying the therapeutic device relative to an anatomical object within an anatomical region,
wherein the delivery section includes a delivery segment operable for sensing a shape and an orientation of the delivery section within the anatomical region relative to a reference element located at a position along the delivery section, and
wherein the delivery segment includes:
an optical fiber including a deformation sensor optic array operable for sensing the shape and the orientation of the delivery section within the anatomical region relative to the reference element; and
an electromagnetic coil for defining the reference element;
a delivery tracking system in communication with the delivery segment to track a position and an orientation of the therapeutic device relative to the anatomical object as a function of a sensed shape and a sensed orientation of the delivery section within the anatomical region relative to the reference element as sensed by the delivery segment; and
an image guiding system in communication with the delivery tracking system to display an image of an orientation of the therapeutic device relative to a plane of the anatomical object derived from at least one of the sensed shape and the sensed orientation of the delivery section within the anatomical region relative to the reference element,
wherein the plane is extracted from within a volume image of the anatomical region excluding the therapeutic device.

8. The image-guided therapeutic device deployment system of claim 7,
wherein the delivery segment is an optical fiber including a deformation sensor optic array operable for sensing the shape and the orientation of the delivery section within the anatomical region relative to the reference element; and
wherein the deformation sensor array defines the reference element.

9. The image-guided therapeutic device deployment system of claim 7, wherein a display of the orientation of the therapeutic valve relative to the plane of the anatomical object includes:
a display of the therapeutic valve relative to the plane of the anatomical object within an X-ray image of the anatomical region.

10. The image-guided therapeutic device deployment system of claim 7, wherein the delivery segment at least partially circumscribes the therapeutic device.

11. The image-guided therapeutic device deployment system of claim 7, wherein a display of the orientation of the therapeutic device relative to the plane of the anatomical object includes:
a display of an orientation axis perpendicular to the plane; and
a display of an angular orientation of a vector relative to the orientation axis, the vector being representative of the position and the orientation of the therapeutic device relative to the anatomical object.

* * * * *